United States Patent [19]

Rosenblatt et al.

[11] Patent Number: 4,504,442

[45] Date of Patent: Mar. 12, 1985

[54] USE OF CHLORINE DIOXIDE GAS AS A CHEMOSTERILIZING AGENT

[75] Inventors: David H. Rosenblatt, Baltimore, Md.; Aaron A. Rosenblatt, New York, N.Y.; Joseph E. Knapp, Pittsburgh, Pa.

[73] Assignee: Scopas Technology Corporation, New York, N.Y.

[21] Appl. No.: 435,331

[22] Filed: Oct. 19, 1982

[51] Int. Cl.$^3$ ............................................. A01N 1/00
[52] U.S. Cl. ........................................ 422/37; 423/477
[58] Field of Search ..................... 426/312, 316, 318; 422/37; 423/477

[56] References Cited

U.S. PATENT DOCUMENTS

| | | | |
|---|---|---|---|
| 2,126,958 | 8/1938 | Guha | 99/154 |
| 2,394,064 | 2/1946 | Hutchinson | 99/192 |
| 2,409,084 | 10/1946 | Vincent | 127/71 |
| 2,482,958 | 9/1949 | Woodward | 99/150 |
| 2,546,568 | 3/1951 | Taylor | 99/150 |
| 2,678,922 | 5/1954 | Stone | 252/187 |
| 2,691,637 | 10/1954 | Waibel | 252/187 |
| 2,701,781 | 2/1955 | De Guevara | |
| 2,903,367 | 9/1959 | Grindrod | 426/316 |
| 3,097,948 | 7/1963 | Ishikawa | 99/80 |
| 3,123,521 | 3/1964 | Westworth et al. | |
| 3,278,447 | 10/1966 | McNicholas | |
| 3,591,515 | 7/1971 | Lovely | 252/187 |
| 4,021,585 | 5/1977 | Svoboda | 426/332 |
| 4,073,888 | 2/1978 | Snyder | 424/149 |
| 4,084,747 | 4/1978 | Alliger | 239/4 |
| 4,104,190 | 8/1978 | Hartshorn | 252/187 |
| 4,247,531 | 1/1981 | Hicks | 422/37 X |
| 4,284,653 | 8/1981 | Shigeoka et al. | 426/312 |
| 4,370,305 | 1/1983 | Affonso | 422/37 X |

FOREIGN PATENT DOCUMENTS 263760  1/1928  United Kingdom .

OTHER PUBLICATIONS

M. M. Beeby and C. E. Whitehouse, A Bacterial Spore Test Piece for the Control of Ethylene Oxide Sterilization, *J. Appl. Bact.*, 28, 349 (1965).

P. M. Borick, The Spore Problem, in *Disinfection*, M. A. Benarde, ed., Marcel Decker, Pub., N.Y. (1970) at pp. 85–102.

W. J. Masschelein, in *Chlorine Dioxide, Chemistry and Environmental Impact of Oxychlorine Compounds*, R. G. Rice, ed., Ann Arbor Science Pub. (1979), at pp. 5–7 and 152–183.

G. M. Ridenour et al., Sporicidal Properties of Chlorine Dioxide, *Water and Sewage Works*, 96, 279 (1949).

C. E. Gutch et al., Failure of Dialysis Concentrate as a Bactericidal Agent, *Proc. Dialysis Transplant Forum*, 234 (1974).

Abdel-Rahman et al., "Toxicity of Alcide"; J. Applied Toxicology; vol. 2, No. 3; 1982; pp. 160–164.

Orcutt et al., "Alcide: An Alternative Sterilant to Peracetic Acid"; Recent Advances in Germfree Research; 1981; Tokyo; Frontispiece & pp. 79–81.

*Primary Examiner*—Barry S. Richman
*Assistant Examiner*—B. P. Heaney

[57] ABSTRACT

The use of gaseous chlorine dioxide to sterilize surfaces, especially the gas impermeable surfaces of implements commonly employed in the medical sciences, such as those formed from porcelain, ceramics, metal, plastics and glass. The contaminated surfaces are contacted with an effective amount of gaseous chlorine dioxide for a time sufficient to kill bacterial spores at a temperature which does not overly exceed ambient temperature.

20 Claims, No Drawings

USE OF CHLORINE DIOXIDE GAS AS A CHEMOSTERILIZING AGENT

BACKGROUND OF THE INVENTION

The continuous introduction into technical use of new materials which cannot be radiation or heat sterilized or sterilized by exposure to liquid systems has necessitated the development of other means of sterilization. A major modern method for this purpose is based on the use of gaseous chemical agents. Such chemical compounds must be employed selectively, however, as only those which kill spores can be classified as chemical sterilizing agents. A wide variety of antimicrobial agents is available, but in most instances they do not kill resistant bacterial spores. Microbiocides are specifically limited to the destruction of the type of organism suffixed by "cide", e.g., bactericide refers to killing of bacteria, fungicide to fungi, viricide to viruses and sporicide to spores, both bacterial and fungal. Since bacterial spores are the most difficult to destroy, only sporicides may be considered synonymous with chemosterilizers. These may be defined as chemical agents which, when utilized properly, can destroy all forms of microbiological life, including bacterial and fungal spores and viruses.

Gaseous ethylene oxide and formaldehyde are used at many hospitals and medical research facilities to sterilize equipment or work areas that cannot be readily heat- or liquid-sterilized. Formaldehyde, if applied in high concentrations, is likely to leave a residue of solid paraformaldehyde. For this reason, it is often avoided in the sterilization of delicate equipment or in situations in which allergic reactions to this substance may occur. Ethylene oxide, which, unlike formaldehyde, penetrates well into porous materials, is strongly absorbed by rubber and by many plastics so that the vapors are not readily eliminated by brief aeration.

The publication of research relating to the mutagenicity and oncogenicity of both ethylene oxide and formaldehyde threatens to lead to severe limitations, if not outright bans, on the use of these compounds as sterilizing agents. The limitations would significantly increase the costs associated with ethylene oxide sterilization.

Apart from its potential health hazards, ethylene oxide is difficult to handle at the concentrations and temperatures required for effective sterilization. Ethylene oxide at a 3–80 percent concentration in air is violently explosive and so ethylene oxide is commonly employed in admixture with an inert gas such as a fluorocarbon, for example, 12 percent ethylene oxide and 88 percent Freon 12 ® (E. I. DuPont Co.). In the sterilization of medical products, temperatures as high as 130°–140° F. are commonly employed to ensure sterility at chamber concentrations of 300–1200 mg/l of ethylene oxide. Prehumidification followed by gas exposure times of at least 4.0 hours are commonly employed. Also, ethylene oxide is more effective in killing dry spores on porous materials, such as paper or fabrics, than on nonporous materials such as glass, ceramics, hard plastics and metals. See C. W. Bruch and M. K. Bruch, *Gaseous Disinfection,* in *Disinfection,* M. A. Benarde, Ed., Marcel Decker, Pub., New York (1970) at pages 149–207.

Chlorine dioxide has long been recognized as being biologically active and early studies indicated that it possesses bactericidal, viricidal and sporicidal properties when applied in aqueous solution at minimum concentrations of about 0.20–0.25 mg/l. See W. J. Masschelein in *Chlorine Dioxide: Chemistry and Environmental Impact of Oxychlorine Compounds,* R. C. Rice, ed., Ann Arbor Science Pub. (1979); G. M. Ridenour, et al., Water & Sewage Works, 96, 279 (1949). However, more recent patents have stated that aqueous chlorine dioxide alone is not sporicidal unless used in the presence of stabilizers. See Snyder, U.S. Pat. No. 4,073,888. Sterilization with aqueous chlorine dioxide suffers from all of the general disadvantages associated with the use of aqueous sterilizing agents, including formulation and handling difficulties, the inability to sterilize moisture-sensitive equipment or substances, and the deposition of residues upon drying.

Little is known of the gas-phase chemistry of chlorine dioxide in air. At concentrations above about 10% (i.e., at about 288 mg per liter), the compound is unstable and sometimes detonates—probably in a shock or light-catalyzed decomposition. For this reason, chlorine dioxide gas cannot be stored. At the same concentration in aqueous solution, it is quite stable.

The chemistry of chlorine dioxide in water is thought to be influenced by the formation of hydrates. At low temperatures (but above 0° C.), high concentrations of chlorine dioxide precipitate out as hydrates of somewhat variable composition; warming permits these to redissolve. It is likely that chlorine dioxide in these warmed solutions still has some water molecules clustered about it. Such hydrates would not, of course, occur in the vapor phase.

In general, both the distance of molecules from one another in the gas phase and the absence of polar solvent effects must profoundly alter the chemistry of chlorine dioxide in air. Finally, only relatively small molecules have sufficient vapor pressure to co-exist with chlorine dioxide. Thus, compounds frequently available for reaction in natural water (e.g., proteins, certain amino acids, humic acids and fulvic acids) would not be found in the vapor state.

Lovely (U.S. Pat. No. 3,591,515) discloses powdered compositions which may be formulated to release 10–10,000 ppm of chlorine dioxide gas. The liberated chlorine dioxide gas is disclosed to be useful to kill bacteria and prevent fungus growth on fruit during shipment.

Due to the handling difficulties associated with chlorine dioxide, the differences in its gas phase and solution chemistry, and the inconsistencies in the above-cited work, chlorine dioxide gas has not been demonstrated to possess utility as a chemosterilizing agent at any concentration.

Accordingly, it is an object of the present invention to utilize chlorine dioxide gas as a chemosterilizing agent, i.e., as a sporicide, for a variety of materials commonly used for medical and dental implements and products.

It is another object of the present invention to utilize chlorine dioxide gas as a chemosterilizer at short exposure times and at ambient temperatures, pressures and relative humidities.

It is another object of the present invention to utilize chlorine dioxide as a chemosterilizing agent for materials such as medical implements which are sealed within gas permeable wrappings.

It is a primary object of the present invention to utilize chlorine dioxide gas as a chemosterilizer for impermeable surfaces, which may be dried prior to sterilization.

Other objects, advantages and novel features of the present invention will be apparent to those skilled in the art from the following description and appended claims.

BRIEF DESCRIPTION OF THE INVENTION

The objects of the present invention are attained by exposing microbiologically-contaminated surfaces, such as those of medical or dental implements, to an atmosphere containing an effective concentration of chlorine dioxide gas. The chlorine dioxide gas acts to sterilize the surfaces at ambient temperatures, pressures and humidities. The effective concentrations of chlorine dioxide gas may be set at a level at which explosion, corrosivity and residue deposition are not significant considerations, and the gas may be used in conjunction with an apparatus in which the possibility of escape of a toxic concentration of chlorine dioxide into the workplace atmosphere is minimized.

DETAILED DESCRIPTION OF THE INVENTION

Chlorine dioxide gas may be prepared by any of the methods known in the art. A preferred method is the disproportionation of sodium chlorite solutions in the presence of acids. In one embodiment of this method a dilute solution of aqueous potassium persulfate is treated with a dilute solution of aqueous sodium chlorite at ambient temperatures, i.e., at 20°–30° C., in a closed reaction vessel. See Rosenblatt, et al., *J. Org. Chem.*, 28, 2790 (1963). The temperature of the chlorine dioxide atmosphere which forms in the space above the stirred reaction mixture may be adjusted by external heating or cooling. The desired amount of chlorine dioxide gas is then admitted into a suitable exposure chamber which preferably has been partially evacuated and which contains the objects to be sterilized. The chlorine dioxide gas is admitted into the exposure chamber in admixture with a carrier gas which is inert to (nonreactive with) chlorine dioxide at the concentrations which are used for sterilization. The final internal pressure may be adjusted, i.e., to one atmosphere or above, with nitrogen, argon or another inert gas. At the end of the exposure period, the exposure chamber is evacuated to remove the chlorine dioxide and flushed with filtered inert gas or air. The evacuated chlorine dioxide may be easily destroyed by passing it through a reducing agent, for example by passing it through a column of sodium thiosulfate chips.

The composition of the chlorine dioxide atmosphere employed for various sterilization runs may be determined colorimetrically by any of the standard methods, for example, by the method of Wheeler, et al., *Microchem. J.*, 23, 168–164 (1978). A sample of the atmosphere inside the exposure chamber is obtained via a septum port using a gas-tight syringe. The volume of the sample is varied depending on the anticipated concentration of chlorine dioxide in the atmosphere. The atmosphere is preferably sampled at the beginning and at the end of the exposure period. The syringe contents are injected into a suitable container, i.e., a cuvette, holding an equal volume of chemicals which react to form a chlorine dioxide concentration-dependent color. After completion of the reaction, the absorbance of the solution at an appropriate wavelength is measured and the concentration of chlorine dioxide determined via a reference curve. This method may generally be adapted to employ any of the well-known colorimetric methods of analyzing for chlorine dioxide.

The spores of the standard test organism employed to determine the effective sterilizing concentration of chlorine dioxide gas were those of *Bacillus subtilis* var. *niger* (ATCC 9372). The dry spores of this organism are known to be extremely resistant to sterilization and have been often used to measure the effectiveness of gas sterilizing agents. See, e.g., P. M. Borick and R. E. Pepper, *The Spore Problem*, in *Disinfection*, M. A. Benarde, Ed., Marcel Decker, Pub., N.Y. (1970) at pages 85–102 and A. M. Cook and M. R. W. Brown, *J. Appl. Bact.*, 28, 361 (1965), the disclosures of which are incorporated herein by reference. Therefore, any given concentration of chlorine dioxide was rated effective as a sterilizing agent if an initial population of $10^5$–$10^7$ spores showed no growth on a nutrient medium after nine days observation following exposure to said concentration.

Standard suspensions of spores of *B. subtilis* var. *niger* were prepared as described by Dudd and Daley in *J. Appl. Bacteriol.*, 49, 89 (1980), which is incorporated herein by reference. Test paper strips for incubation were prepared by adding 0.2 ml of a methanolic suspension of the spores to $7 \times 35$ mm strips of presterilized Whatman 3 mm paper in glass Petri dishes. The papers were vacuum-dried (30 min at 30° C. and 30 in. Hg.) and kept at ambient temperature and humidity (20°–30° C., 40–60 percent relative humidity) prior to use. The spore load on each strip prepared in this way was $1.4 \times 10^6$ spores.

Metal foil test pieces were prepared by fashioning $18 \times 28$ mm square of aluminum foil into small cups. These were sterilized in glass Petri dishes. To each cup was added 0.2 ml of a methanolic suspension of the spores. The cups were dried at ambient temperature and held at ambient temperature and humidity prior to use. The spore load on each cup was approximately $1.4 \times 10^6$ spores.

Foils and paper strips in glass Petri dishes were placed in an exposure chamber and exposed for up to 1.0 hour to various concentrations of chlorine dioxide gas in nitrogen. Typically 4–6 replicates of each were run at one time. A range of gas concentrations was utilized in order to determine effective sterilizing concentrations for each surface.

After exposure, the paper strips were transferred to individual tubes of a sterile, growth promoting medium, and observed for growth at appropriate intervals. The aluminum foil cups were shaken with glass beads in water to dislodge the spores. The spore suspension was then contacted with suitable media preparations and observed for growth. If no growth was observed after the incubation period, a condition of sterility was ascribed to the exposed materials.

It was found that exposure of the paper strips to concentrations as low as about 40 mg/l of chlorine dioxide gas at a temperature of about 27° C. and a relative humidity of about 60 percent for about one hour resulted in reproducible sterilization of the strips, i.e., no spore growth was observed after a nine day incubation period. Surprisingly, in view of the behavior of ethylene oxide the spores proved to be no more resistant when exposed on aluminum. Concentrations of chlorine dioxide gas of as low as about 35 mg/l resulted in reproducible sterilization of the foil cups. For each material, sterility was achieved in a number of runs after exposure to lower concentrations of chlorine dioxide, including concentrations as low as 11 mg/l.

The practice of the invention will be further illustrated by reference to the following detailed examples.

EXAMPLE 1

A 1000 ml 2-necked round-bottomed flask was equipped with a dropping funnel and magnetic stirring was employed as a reaction vessel. An inlet tube for nitrogen gas equipped with a glass wool filter and a needle valve was positioned so that nitrogen could be admitted below the surface of the reaction mixture. An outlet tube was equipped with a needle valve and positioned so that gas could be allowed to pass from the top of the reaction vessel into the exposure vessel.

A 2000 ml glass reaction kettle equipped with a septum-capped port, a manometer, and inlet and outlet ports was employed as the exposure vessel. The outlet tube of the 1000 ml flask was connected to the inlet port of the incubation vessel.

In a typical run the 1000 ml flask was charged with 100 ml of a 8 percent aqueous sodium chlorite solution under nitrogen. All of the valves were closed and a solution of 2.0 g potassium persulfate in 100 ml of water was added dropwise with stirring. The reaction mixture was stirred for 30–45 minutes at 27° C. to complete the generation of the chlorine dioxide gas.

The exposure chamber was loaded with 3-6 spore-coated paper strips or aluminum foil cups, each contained in an individual glass Petri dish. The chamber was swept with nitrogen, closed and then evacuated (30 in. Hg). The outlet valve on the tube leading from the reaction vessel was opened and the amount of chlorine dioxide gas admitted from the reaction vessel was controlled by following the increased pressure readings on the manometer. The outlet valve was closed and the pressure in the exposure vessel was then brought to one atmosphere by admission of nitrogen.

The atmosphere in the exposure vessel was immediately sampled by removal of 0.5–2.0 ml of the atmosphere by means of a gas-tight syringe via the septum. The chlorine dioxide concentration was determined by the method of Wheeler, et al., *Microchem. J.*, 23, 160 (1978). After 60 minutes had elapsed the atmosphere was sampled again. The exposure chamber was then evacuated and refilled with filtered air. The evacuation and refilling steps were repeated, the chamber was opened and the contents removed under sterile conditions.

The paper strips were aseptically transferred to individual tubes of typticase soy broth and incubated at 37° C. Observations to determine the presence or absence of spore growth were made after 24 and 48 hours. Those tubes which did not show growth after 48 hours were incubated for one week and observed every 24 hours. If no growth was observed after one week, the strip was recorded as negative, or sterilized.

After exposure, the foils were transferred into individual tubes containing 20 ml of sterile water and a few glass beads. After vigorous shaking to dislodge and suspend the spores, 0.1 ml of the suspension was placed in duplicate on a plate of typticase soy agar. The plates were incubated at 37° C. and observed as described above for the paper strips. Appropriate control strips and foils were run for these determinations. The outcome of eighteen specific runs is summarized on Table I as Examples 2–19.

TABLE I

CHLORINE DIOXIDE STERILIZATION

| Example | Chlorine Dioxide (MG/L) | Results* Strips | Results* Foil Cups |
|---|---|---|---|
| 2 | 11 | 0/6 | 0/6 |
| 3 | 12 | 0/6 | 0/6 |
| 4 | 25 | 0/6 | 0/6 |
| 5 | 31 | 1/6 | 0/6 |
| 6 | 34 | 0/6 | 5/6 |
| 7 | 35 | 1/6 | 0/6 |
| 8 | 40 | 0/6 | 0/6 |
| 9 | 41 | 0/6 | 0/6 |
| 10 | 44 | 0/5 | 0/6 |
| 11 | 45 | 0/6 | 0/6 |
| 12 | 46 | 0/6 | 0/6 |
| 13 | 65 | 0/6 | 0/6 |
| 14 | 69 | 1/6 | 0/6 |
| 15 | 78 | 0/6 | 0/6 |
| 16 | 84 | 0/6 | 0/6 |
| 17 | 94 | 0/6 | 0/6 |
| 18 | 98 | 0/6 | 0/6 |
| 19 | 113 | 0/6 | 0/6 |

*Exposure time - 1 hr. Results in number of strips or cups on which growth is observed/number of strips or cups exposed.

The results of Examples 2–19 demonstrate that a chlorine dioxide concentration of at least 40 mg/l is effective to sterilize paper strips contaminated with dry *B. subtilis* spores, and thus, presumably, to kill any other microorganisms present. The scattered incidences of growth observed in Exs. 5, 7 and 14 may be largely discounted as due to random experimental error. It is expected that more rigorous control of the laboratory procedures and of the biological standards would demonstrate effective sterilization over the complete range of gas concentrations employed. Similar concentrations would be expected to sterilize other types of porous organic surfaces, such as rubber, gas permeable plastic, sponge, plant material, wood and the like, without causing appreciable decomposition or residue deposition.

A concentration of chlorine dioxide of at least 35 mg/l is adequate to sterilize aluminum foil contaminated with dry spores. The growth observed on foil in Ex. 6 is probably due to a random experimental error, since a range of lower gas concentrations consistently resulted in sterilization. These results lead to the expectation that other nonporous surfaces normally impermeable to gas sterilizing agents would be readily sterilized under similar conditions, such as those of medical or dental instruments or implements formed from metals such as stainless steel, plated steel, aluminum and nickel or from nonporous plastics, porcelain, ceramics, or glass.

Chlorine dioxide gas has also been successfully employed to sterilize commercially-available spore strips which are sealed in gas-permeable paper envelopes. A procedure which may be used to sterilize such materials is described below.

EXAMPLE 20

Six Spordi ® paper spore strips (American Sterilizer Corp., Erie, Pa.), each containing a mixture of spores of *B. subtilis* and *B. stearothermophilus* (NCTC 10003) and each enclosed in a sealed, sterile envelope of glassine paper are exposed to atmospheres containing 50 and 100 mg/l of chlorine dioxide gas as described in Example 1. The sealed spore strips are removed from the exposure chamber, opened under sterile conditions and incubated as described in Example 1. Growth levels are observed after nine days of incubation which indicate that the strips are effectively sterilized under these conditions.

It is therefore expected that chlorine dioxide will effectively sterilize contaminated surfaces which are sealed in gas permeable container materials such as coated and uncoated paper, plastic sheeting, and the like without significantly reacting with the container materials. The ability of effective concentrations of chlorine dioxide to readily permeate such enclosures would find application in the sterilization of medical products which are preferably sterilized after packaging so as to be maintained in a sterile condition during shipping and storage.

Thus, it has been demonstrated that chlorine dioxide gas is an effective chemosterilizer for a variety of dry surfaces under conditions of ambient temperature, pressure and humidity. Surfaces sealed in gas permeable materials are also sterilized effectively under these conditions. Although effective concentrations for sterilization are suggested by the procedures of the above examples, one would except that lower concentrations would also be effective to sterilize the materials involved.

While certain representative embodiments of the present invention have been shown for the purpose of more particularly illustrating the invention, it will be apparent to those skilled in the art that various changes or modifications may be made therein without departing from the scope and spirit of the invention.

We claim:

1. A method of sterilizing comprising contacting gas impermeable surfaces contaminated with bacterial spores with an effective amount of gaseous chlorine dioxide wherein said contacting is performed at a temperature which does not overly exceed ambient temperature and for at time period sufficient to kill the bacterial spores on said contaminated surface.

2. The method of claim 1 wherein said bacterial spores comprise spores of *B. subtilis* var. niger.

3. The method of claim 1 wherein said impermeable surfaces are formed of materials selected from the group consisting of metals, glass, porcelain, or gas-impermeable plastics.

4. The method of claim 3 wherein the surfaces of medical or dental implements are sterilized.

5. The method of claims 1, 2, 3 or 4 wherein the surfaces are contacted with an atmosphere containing at least about 11 mg/l of chlorine dioxide.

6. The method of claim 5 wherein the atmosphere contains at least about 40 mg/l of chlorine dioxide gas.

7. The method of claim 5 wherein the atmosphere further comprises an inert gas.

8. The method of claim 7 wherein the inert gas is nitrogen.

9. The method of claims 1, 2, 3 or 4 wherein the chlorine dioxide is contacted with the surfaces at ambient temperature, pressure, and humidity.

10. The method of claim 9 wherein the contact time is at least about one hour.

11. The method of claims 1, 2, 3 or 4 wherein the surfaces are dried prior to sterilization.

12. The method of claims 1, 2, 3 or 4 wherein the surfaces are enclosed in a gas permeable material prior to sterilization.

13. The method according to claim 1 wherein said temperature is about 20° C. to about 30° C.

14. The method of claim 1 wherein said impermeable surfaces are formed of ceramic material.

15. A method for sterilizing gas impermeable surfaces contaminated with bacterial spores comprising:
    (a) drying said gas impermeable surfaces;
    (b) removing substantially all of the air from contact with the surfaces;
    (c) contacting the surfaces for at least about one hour with an atmosphere consisting of a sterilizing amount of chlorine dioxide gas in admixture with an amount of inert gas sufficient to adjust the pressure of the gas mixture to about one atmosphere wherein said contacting is performed at a temperature not overly exceeding room temperature and for a time period sufficient to kill said bacterial spores.

16. The method of claim 15 wherein an atmosphere comprising at least about 11 mg/l of chlorine dioxide gas is employed.

17. The method of claim 14 wherein the materials are selected from the group consisting of metals, glasses, porcelains, or plastics.

18. The method of claim 17 wherein the surfaces of medical or dental implements are sterilized.

19. The method of claims 15 or 18 further comprising enclosing the surfaces in a gas permeable material prior to step (b).

20. The method of claim 15 wherein said impermeable surfaces are formed of ceramic material.

* * * * *